United States Patent
Kaminsky

[11] 3,936,563
[45] Feb. 3, 1976

[54] HYDROXYMETHYLENE-SUBSTITUTED CHROMONE-3-CARBOXALDEHYDES, PROCESS FOR THEIR PREPARATION AND INTERMEDIATES PRODUCED THEREBY

[75] Inventor: Daniel Kaminsky, Parsippany, N.J.

[73] Assignee: Warner-Lambert Company, Morris Plains, N.J.

[22] Filed: Dec. 20, 1974

[21] Appl. No.: 534,599

Related U.S. Application Data

[62] Division of Ser. No. 352,134, April 18, 1973, Pat. No. 3,879,426.

[52] U.S. Cl. .............................................. 424/283
[51] Int. Cl.² ........................................ A61K 31/35
[58] Field of Search .................................. 424/283

[56] References Cited
UNITED STATES PATENTS

| | | | |
|---|---|---|---|
| 3,786,071 | 1/1974 | Cairns | 424/283 |
| 3,816,470 | 6/1974 | Tronche | 424/283 |

*Primary Examiner*—Norman A. Drezin
*Attorney, Agent, or Firm*—Albert H. Graddis; Frank S. Chow; Anne M. Kelly

[57] ABSTRACT

Novel (hydroxymethylene) chromone derivatives of the general formula I:

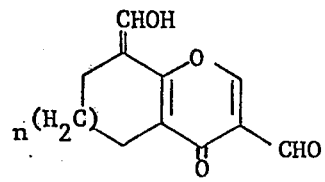

wherein $n$ represents 1 or 2, are prepared by reacting a cycloalkanone II with a boron trifluoride compound and acetic anhydride to obtain novel boron complex intermediates of the formula III:

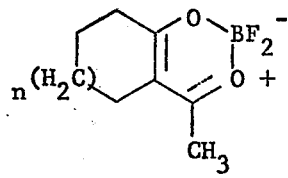

wherein $n$ represents 1 or 2, and reacting III with a Vilsmeier reagent prepared from phosphorus oxychloride and dimethylformamide. The final product I and pharmaceutical compositions containing I are useful in the treatment of allergic conditions and in the treatment of hyperacidity.

1 Claim, No Drawings

HYDROXYMETHYLENE-SUBSTITUTED CHROMONE-3-CARBOXALDEHYDES, PROCESS FOR THEIR PREPARATION AND INTERMEDIATES PRODUCED THEREBY

This is a division, of application Ser. No. 352,134 filed April 18, 1973, now U.S. Pat. No. 3,879,426.

According to the novel process of this invention, novel compounds of the general formula I:

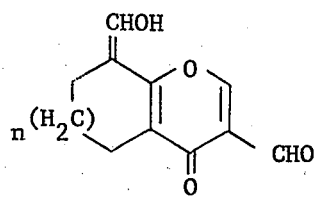

wherein $n$ represents 1 or 2, are prepared by reacting a cycloalkanone of the formula II:

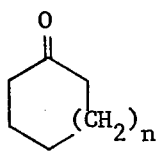

wherein $n$ represents 1 or 2, with a boron trifluoride compound and acetic anhydride to obtain novel intermediates of the formula III:

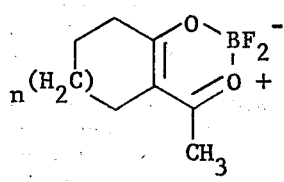

wherein $n$ represents 1 or 2, and reacting intermediate III with an excess of a Vilsmeier reagent prepared from phosphorus oxychloride and dimethylformamide. Quite surprisingly, novel compounds of formula I having a hydroxymethylene substituent on the saturated ring are obtained. When a 6-membered starting ketone is used, the hydroxymethylene group forms on position 8 of the final compound I; when a 7-membered starting ketone is used, the hydroxymethylene substituent forms on position 9 of the final compound I.

The starting cycloalkanones II used in the novel process of this invention are commercially available. The boron trifluoride compound used is preferably boron trifluoride etherate. In the second step of the process reaction, an excess of Vilsmeier reagent is reacted with the boron complex intermediate III.

Compounds of this invention having the general formula I above have been found to reduce histaminic responses to antigen challenge by inhibiting antibody-antigen reactions in mammals such as rats or guinea pigs upon oral or parenteral administration. When tested in accordance with the procedure of Mota, Life Sciences, 7, 465, (1963) and Ovary, Proc. Soc. Exptl. Biol. Med., 81, 584, (1952), therapeutic compositions containing the compounds of this invention are effective at dosages of 5 mg to 50 mg/kg of body weight.

Pharmaceutical compositions containing the compounds of this invention are therefore useful in the management of allergic reactions such as bronchial asthma. To treat bronchial asthma, a dose of 5 mg to 50 mg/kg by injection or by aerosol administration is suggested. The dosage may be varied depending upon severity of the condition and the weight, age and sex of the patient being treated.

In use, the compounds of this invention may be combined with a parenterally acceptable vehicle, such as a gum tragacanth saline suspension, to provide dosage forms suitable for parenteral administration; or they may be combined with pharmaceutical diluents such as lactose, cornstarch, and the like and formulated into tablet or capsule dosage forms. In order to enhance their therapeutic spectrum, the compounds of this invention may be combined with sympathomimetic agents such as isoprenaline or combined with steroids such as cortisone and its derivatives.

The compounds of this invention also exhibit antisecretory effects and are therefore useful in relieving gastric hyperacidity. Gastric hyperacidity has generally been described as a factor which contributes to peptic ulcer. The compounds of this invention, when administered to mammals in a manner as described below, have been found to inhibit the gastric secretion of hydrochloric acid and are therefore effective in reducing the resulting acidity in the stomach.

At a dosage of 20 mg/kg administered intraperitoneally, the subject compositions are effective in reducing gastric acidity in the pylorus ligated rat when tested according to the procedure of H. Shay, Gastroenterology, 5, 43, (1945).

Pharmaceutical compositions containing the compounds of this invention, are thus indicated in the management of gastric hyperacidity and the treatment of peptic ulcer resulting from such hyperacidity. For parenteral administration, the pharmaceutical composition of this invention may be administered as aqueous suspensions for intramuscular injection. These are prepared, for example, by suspending the active ingredient in sterile water and packaging in ampules so as to provide a concentration of 1,000 mg of the active ingredient per dosage unit.

Generally speaking, the dose required to effectively relieve gastric hyperacidity is within the range of 20 mg/kg of body weight of the mammal being treated. This dosage regimen may be varied depending upon the condition of the patient.

Novel boron complex intermediates having the formula III, are useful in preparing the pharmacologically active final compounds having the formula I above.

To further illustrate the practice of this invention, the following examples are included:

EXAMPLE 1

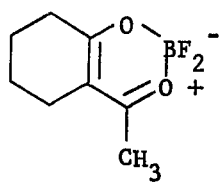

Preparation of 2,2-difluoro-5,6,7,8-tetrahydro-4-methyl-1,3,2-benzodioxaborin 144.8 Grams of cyclohexanone in 360 ml of acetic anhydride is added, dropwise, to 217 ml of BF₃ etherate. The reaction is slightly exothermic. The reaction solution is stirred and the temperature is maintained at about 35°C for 1 hour, then cooled and titurated with ether. After standing overnight a solid precipitates and is filtered. The filtrate is concentrated and the residue is reacted with warm ether (Florisil). The addition of Skellysolve B causes precipitation of additional solid. Total yield is 128 grams, 45.4%, m. p. 77°–78°C.

Anal. Calcd. for $C_7H_{11}BF_2O_2$: C, 51.12; H, 5.90; F, 20.21. Found: C, 51.09; H, 5.95; F, 20.21.

EXAMPLE 2

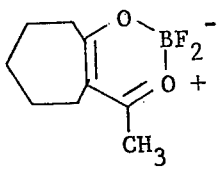

Preparation of 2,2-difluoro-6,7,8,9-tetrahydro-4-methyl-5H-cyclohepta[e]-1,3,2-dioxoborin.

100 Grams of cycloheptanone in 195 ml of acetic anhydride is added, dropwise, to 117 ml of boron trifluoride etherate. The reaction is slightly exothermic (35°C) and the solution is stirred with maintaining this temperature for 1.5 hours, by heating on a steam bath (vapor evolution) for 1 hour. The reaction is cooled and triturated with a little ether (100 ml). After standing overnight, a solid precipitates which is filtered. The filtrate is concentrated and the residue is extracted with warm ether (Florisil). The addition of Skelly B causes precipitation of additional solid. Total yield is 110 grams, 60.5%. Recrystallized from ether/Skelly B, three times gives light yellow crystals, dried, vac., 25°C, 7 hours, m. p. 84°–86°C.

Anal. Calcd. for $C_9H_{13}BF_2O_2$: C, 53.51; H, 6.49; F, 18.81. Found: C, 53.25; H, 6.69; F, 18.63, 18.56.

EXAMPLE 3

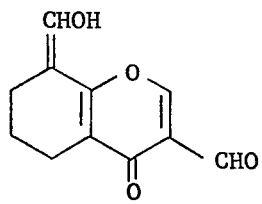

Preparation of 5,6,7,8-tetrahydro-8-(hydroxymethylene)-4-oxo-4H-1-benzopyran-3-carboxaldehyde 100 grams of the boron complex of Example 1, (2,2-difluoro-5,6,7,8-tetrahydro-4-methyl-1,3,2-benzodioxaborin), is added to the Vilsmeier reagent prepared from 200 ml of phosphorus oxychloride and 500 ml of dimethylformamide at 0°C, with stirring for about 10 minutes. The reaction is initially, exothermic. After 10 minutes, it is heated on a steam bath for 2 hours and then poured into about 2 liters of ice water and stirred for 4 hours. A solid precipitates which is filtered, triturated with CH₃CN, filtered and dried to give 43.2 g (21%) of product. The product is recrystallized from aqueous dimethylformamide to give a light tan crystalline product, mp 226.8°C (dec.).

Anal. Calcd. for $C_{11}H_{10}O_4$: C, 64.08; H, 4.89; O, 31.04. Found: C, 64.22; H, 4.89; O, 30.80.

EXAMPLE 4

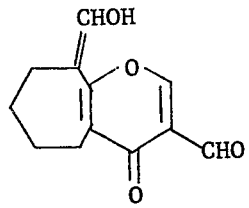

Preparation of 4,5,6,7,8,9-hexahydro-9-(hydroxymethylene)-4-oxo-cyclohepta[b]pyran-3-carboxaldehyde To 140 ml of dimethylformamide at 0°C, there is added, dropwise, 61.2 g (0.4 mol) of phosphorus oxychloride. To this solution is added 20.2 g (0.1 mol) of the boron difluoride complex prepared in Example II. The solution is heated on a steam bath for 3 hours and is poured into 1 liter of ice water. A solid precipitates, is filtered and washed with acetone to give 10.2 g (46%) of brown solid. Recrystallization from aqueous dimethylformamide gives a greyish-brown powder, m.p. 202°–203°C (dec.).

Anal. Calcd. for $C_{12}H_{12}O_4$: C, 65.44; H, 5.49. Found: C, 65.38; H, 5.33.

I claim:

1. A method for preventing asthmatic symptoms which comprises administering to a mammal in need thereof from 5 to 50 mg/kg of body weight of a compound having the formula:

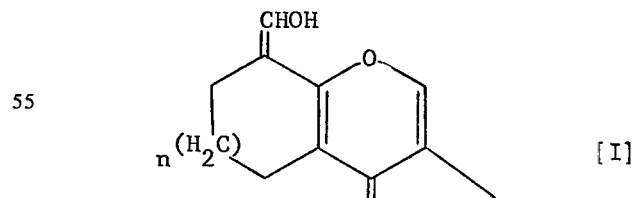

wherein $n$ represents 1 or 2.